United States Patent [19]

Silver

[11] Patent Number: 4,606,420

[45] Date of Patent: Aug. 19, 1986

[54] APPARATUS WITH FORCE ISOLATION FOR MEASURING WEIGHT OF COLLECTED FLUID AND METHOD

[75] Inventor: Brian H. Silver, Hoffman Estates, Ill.

[73] Assignee: The Kendall Company, Boston, Mass.

[21] Appl. No.: 730,740

[22] Filed: May 6, 1985

[51] Int. Cl.[4] .......................... G01G 19/00; A61B 5/00
[52] U.S. Cl. .................................. 177/160; 177/245; 128/771; 141/83
[58] Field of Search .............. 177/160, 165, 245, 263; 248/99–101; 128/771, DIG. 13; 141/83

[56] References Cited

U.S. PATENT DOCUMENTS

| | | | |
|---|---|---|---|
| 3,353,572 | 11/1967 | Anderson et al. | 141/83 X |
| 4,305,405 | 12/1981 | Meisch | 128/771 X |
| 4,317,550 | 3/1982 | Hannah | 248/95 |
| 4,417,585 | 11/1983 | Frank | 128/771 X |

Primary Examiner—George H. Miller, Jr.

Attorney, Agent, or Firm—James W. Potthast

[57] ABSTRACT

A urinary output monitor for determining the volume of fluid in a urinary collection bag during the collection process having a weighing apparatus for weighing the contents of a collection bag and means for substantially isolating the end of a drainage tube from applications of significant forces to the collection container. The isolation mechanism is incorporated into the container assembly in the form of a conduit for interconnecting an inlet connector and an outlet connector which has sufficient flexibility to preclude it from conveying any significant force in a direction along its length which would adversely affect the weight measurement. Since varying forces applied to the weighing apparatus by drainage tube connectors of different catheters are eliminated by the isolation mechanism, fluid entered after offset determination for zeroing the weighing apparatus to compensate for bag weight is included in the total measurement.

26 Claims, 18 Drawing Figures

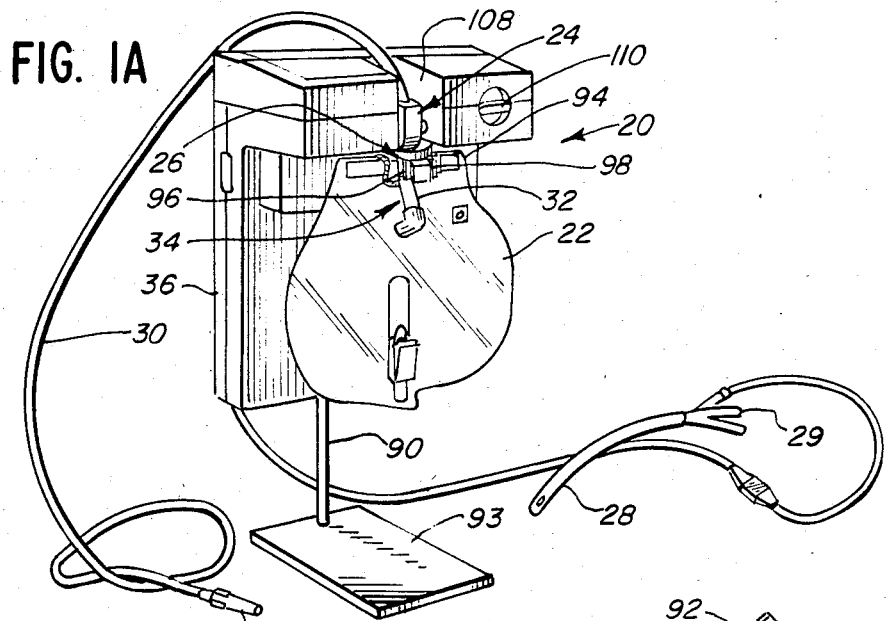
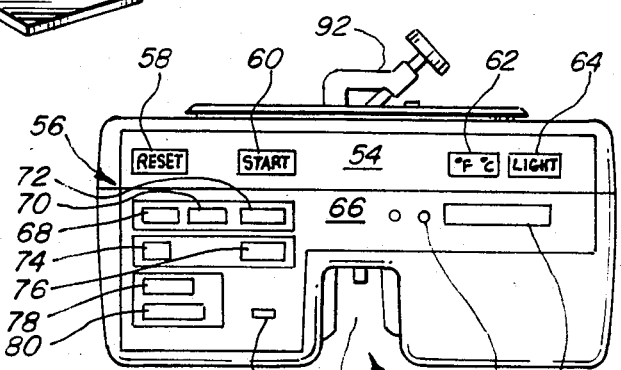
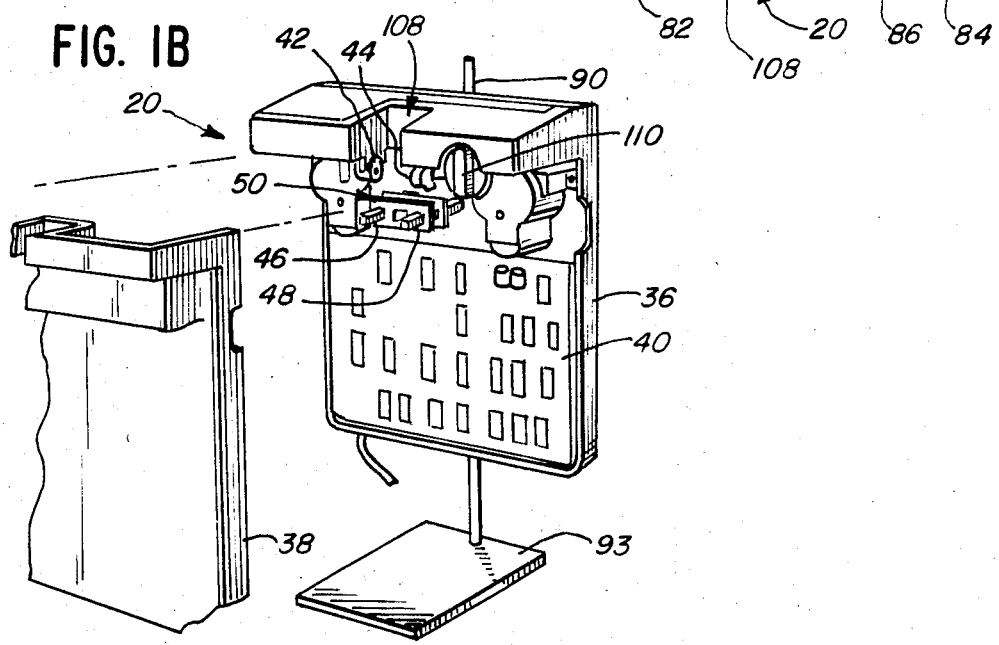

APPARATUS WITH FORCE ISOLATION FOR MEASURING WEIGHT OF COLLECTED FLUID AND METHOD

BACKGROUND OF THE INVENTION

This invention relates to apparatus for weighing collected fluid during the collection process and, more particularly, to means for isolating the weighing mechanism from coupling forces of the fluid collection system and a method of using same to obtain improved accuracy in weight measurements.

Various apparatus are known for determining the urinary output of a patient which is measured in units of volume. In U.S. Pat. No. 4,448,207 of Parrish, the height of fluid in a collection container is determined through ultrasonic echo sensing, and then the volume is calculated by a computer based upon a stored volumetric profile of the collection container and the determined height. Similarly, in U.S. Pat. No. 4,051,431 of Wurster, the level of a fluid in a container is determined by means of capacitive sensing from which the volume can be determined in a rigid container. In U.S. Pat. No. 4,314,484 of Bowman, an optical drop count apparatus first forms drops from the collected fluid of approximately a known uniform volume and then counts the drops to determine the total volume accumulated. A similar apparatus is also shown in U.S. Pat. No. 4,291,692 of Bowman et al., 4,347,316 of Jesperson and 4,286,590 of Murase.

Other techniques of measurement are also known. In U.S. Pat. No. 4,417,585 of Franck, moveable measurement containers are alternately filled and dumped in a collection container, and the volume is calculated by measuring the number of fill and dump cycles. Similarly, in U.S. Pat. No. 4,206,767 of Winegrove, a plurality of measurement tubes are successively filled and sensed to determine volume.

It has also been known to weigh the collected fluid and to determine the volume from the weight. The weight and thus volume is determined in U.S. Pat. No. 3,583,400 of Menhardt by means for moving the collection fluid and determining the momentum of the fluid from which the mass of collected fluid is calculated. In an article by N. J. Randall, entitled "A New URO Flowmeter for Routine Clinical Use" in the January, 1975 issue of Biomedical Engineering (London), a simple strain gauge transducer system associated with a cantilever beam is employed to make direct weight measurements. A special tube is provided to absorb and redistribute urine flow into the container to prevent momentum during flow from effecting the weight measurement.

It is also known to use the weight measurements of collected fluid to control the fluid collection process itself. For instance, in U.S. Pat. No. 3,583,400 of Menhardt, a switch controls fluid flow in a collection container in resonse to measurement of collected fluid. Weight is used to stop a blood collection process when the amount collected exceeds a preselected weight in an apparatus shown in U.S. Pat. No. 3,977,567 of Rudd. In U.S. Pat. No. 4,390,073 of Rosen, blood in a collection bag is weighed to control collection.

While other approaches for work, the measurement of weight to determine volume is preferred. However, volumentric measurements based on weighing the collected fluid chamber can be no more accurate than the accuracy of the weight measurement itself. Therefore, it is important to make sure that it is only the weight of the fluid being measured and not the weight of the container or the forces associated with the collection system connected with the container which can affect the weight measurement. One of the advantages that weighing has over other methods of volume measurement is that the measurement does not require a special rigid container for level sensing and can be used after collection has commenced or after it is complete. In known systems which measure volume, however, because of the accuracy problem caused by variable forces applied by the upstream collection systems attached to the container, initial amounts of fluid collected in a bag upon catherization and before the bag is attached to the weighing apparatus are not measured in order to zero the weighing apparatus. This is done to partially offset some of the error introduced by the error producing forces applied by the force isolation system against the container.

SUMMARY OF THE INVENTION

It is therefore the primary object of the present invention to provide apparatus with a forced isolation system that overcomes the aforementioned problems with known weighing apparatus and a method of using same to measure all collected fluid including the fluid collected before attachment of the collected fluid container to the weighing apparatus.

The objective is partially achieved through provision of an apparatus for measuring the weight of fluid entering a container of a system obtained from the downstream end of a fluid drainage tube including means for substantially mechanically isolating the end of the tube from the collection container. This apparatus includes a weighing apparatus having a frame and a weighing mechanism which moves relative to the frame during changes of the weight being weighed thereby and means for connecting the container to the weighing mechanism to be weighed thereby. The container moves with the weighing mechanism relative to the frame as increasing amounts of fluid are introduced into the container. Means are provided for holding the downstream end of the tube against movement relative to the frame and for coupling the drainage tube with the container for relative fluid communication therewith. This coupling means includes means for substantially mechanically isolating the end of the tube from application of significant force to the container whereby the accuracy of the measurement of the weight of the container and its contents is not significantly affected by the coupling means.

In a preferred embodiment, the isolation means includes a flexible member interconnecting the end of the drainage tube to the container which is not capable of transferring any force therebetween of any significance. The container can be a flexible bag and includes means attached to one of the pair of connectors for suspending it from the weighing mechanism to move therewith.

The objective of the invention is also achieved through provision of a container assembly for biological fluids, comprising, a hollow container body having an inlet opening for receipt of fluids therewithin, an inlet connector for connection with the end of a drainage tube, and means for substantially mechanically isolating the container body at the inlet opening from relative movement of the inlet connector. The isolating means includes a flexible conduit for interconnecting the inlet connector and inlet opening, and the conduit has a flexibility sufficient to prevent it from mechanically conveying significant force in a direction along the conduit.

Because of the improved accuracy obtained through isolation, an improved method of measuring the total volume of all the fluid collected into a collection container, including that fluid collected before attachment to the weighing mechanism, is provided. This method comprises the steps of predetermining the weight of a fluid container, offsetting the determined weight of the container from a weighing apparatus to zero the weighing apparatus, connecting the downstream end of a drainage tube to an inlet opening of the fluid container by means for substantially mechanically isolating the container and the weighing apparatus from forces due to the interconneciton of the container and the end of the tube, attaching the container to the weighing apparatus to be weighed thereby, entering into the container the fluid to be weighed through the drainage tube and said isolation means and weighing the container and fluid therein. Preferably, the method also includes the steps of entering some of the fluid into the container after determining the amount of offset to zero the weighing apparatus to compensate for the weight of the container and before the step of attaching the container to the weighing apparatus to be weighed thereby and then obtaining from the weighing apparatus the combined weight of the fluid entered into the container before and after the step of attaching the container to the weighing apparatus prior to further zeroing of the weighing apparatus.

BRIEF DESCRIPTION OF THE DRAWINGS

The foregoing objects, features and advantages of the present invention will be described in greater detail and further objects and advantageous features will be made apparent in the following detailed description of the preferred embodiment which is given with reference to the several figures of the drawing, in which:

FIG. 1A is a perspective view of an automated urine output monitor, or AUOM, for weighing and making other measurements of urine collected in a flexible urinary collection bag releasibly attached thereto and with respect to which a preferred embodiment of the present invention is employed;

FIG. 1B is another perspective view of the AUOM of FIG. 1A but with the urinary collection bag and a front panel removed to facilitate a better view of the inner workings of the AUOM;

FIG. 2 is a plan view of the AUOM of FIGS. 1A and 1B showing the AUOM display and control panel;

DETAILED DESCRIPTION

Figure 12:
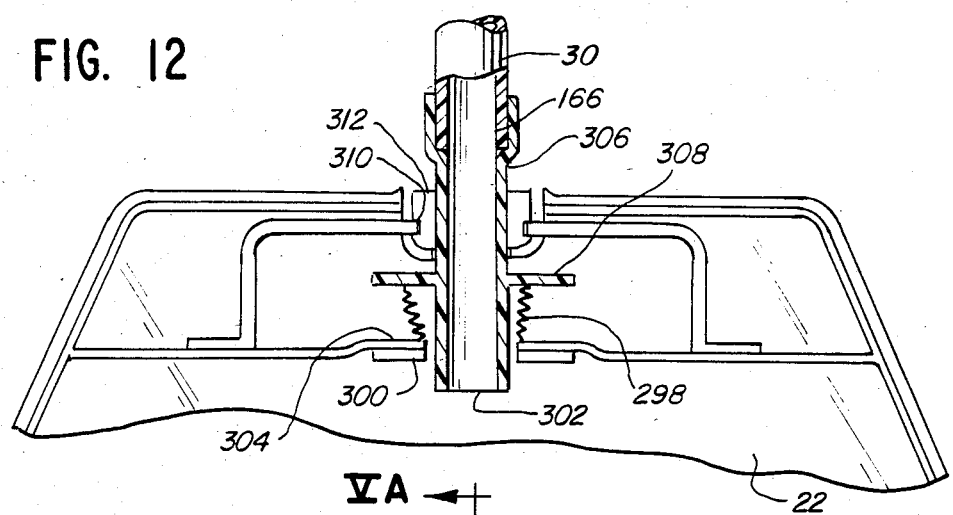
FIG. 12 is a sectional side view of an alternate embodiment of the force isolation system.

Referring now to the several figures of the drawing, particularly FIGS. 1A, 1B and 2, an automated urine output monitor, or AUOM, 20 is seen with a flexible, plastic urinary collection bag mounted thereto by means of a sampling chamber assembly 24 and a force isolation system 26. As will be explained in greater detail, the sampling chamber assembly 24 and force isolation system 26 interconnect to form a closed fluid collection system between a patient (not shown) connected to the distal end of a Foley catheter 28 and the interior of the urinary collection bag 22. The catheter 28 is connectable by means of a catheter connector 29 and connector 31 with flexible, plastic drainage tube 30. The other end of the drainage tube 30 is in fluid communication with the sampling chamber assembly 24 by means of a suitable tube connector located atop sampling chamber assembly 24. Fluid from sampling chamber 24 flows through a flexible conduit of the force isolation system 26 and through an angular conduit 32 of a front entry connector assembly 34.

Referring to FIG. 1B, the AUOM is seen to have a housing, comprised of a housing frame 36 with a removable front housing panel 38. This housing protectively encloses an electronic control and measurement module 40 which includes a computer and interface circuitry. The computer receives signals through the interface circuitry from suitable transducers associated with sensor probe assemblies 42 and 44 connectible with the sampling chamber assembly 24 for noninvasively determining both specific gravity and temperature of a urine sample contained within the chamber assembly 24. The computer is also responsive to electronic signals received through other interface circuitry from transducers associated with a pair of mounting arms 46 and 48 of a bag mounting assembly 50 to determine the weight of the urine collected within urinary collection bag 22. The computer also determines core temperature based on signals from a temperature transducer associated with a core temperature probe within catheter 28 and connected thereto by means of an electrical cord 52. The computer also receives signals through suitable transducers indicative of the ambient temperature, the status of its D.C. portable battery supply (not shown) and signals from a control section 54 of a control and display panel 56, FIG. 2. These controls include a manually actuatable reset switch 58, a start switch 60, a temperature scale selection switch 62 and a display light actuation switch 64.

Referring to FIG. 2, the computer automatically, periodically calculates specific gravity, temperature, volume and time based upon these transducers and control input signals and causes them to be visually indicated at various electronic digital display units of a display section 66 of control and display panel 56. The volume in milliliters of the urine collected in bag 22 for the present hour, the previous hour and for all collection accumulated is indicated at display units 68, 70 and 72. Based upon appropriate signals received from either the start switch 60 or reset switch 58, and an internal clock, the computer also indicates the number of minutes elapsed since the present hour commenced and the cumulative time since the collection process started at display units 74 and 76, respectively. The specific gravity is shown on display unit 78, and core temperature, either in Fahrenheit or centigrade degrees depending upon the state of scale selection switch 62, is shown at display unit 80. A low battery condition for the portable AUOM is provided by an indicator 82, and various conditions sensed by the computer are indicated by an alpha numeric message display unit 84 and an alert indicator lamp 86.

Further information concerning the operation of the computer, transducers and other aspects of the AUOM unit 20 may be obtained by reference to the U.S. patent application of Brian H. Silver entitled "Electronic Biological Fluid Output Monitoring With Noninvasive Sensing", U.S. patent application of Frank W. Ingle and Alan R. Selfridge entitled "Biological Fluid Specific Gravity Monitor with Ultrasonic Sensor Circuit", and U.S. patent application of Fred Rasmussen entitled "Ultrasonic Sensor", all filed contemporaneously herewith and assigned to the assignee of this application.

In normal operations, the AUOM unit is releasibly attached to an upright mounting standard 90 by means of a screw clamp 92 attached to the back of housing 22. Although standard 90 may be mounted to its own floor supported base member 93, as shown, preferably standard 90 is releasibly mounted to the patient's bed in a manner shown in U.S. patent application of James R. Gross, entitled "Medical Equipment Mounting Apparatus" filed contemporaneously herewith and assigned to the assignee of this application.

The catheter set, consisting of catheter 28, catheter drainage tube 30, sampling chamber assembly 24, force isolation system 26, front entry connector assembly 34 and collection bag 22 are brought to the patient and the patient is catherized. After the AUOM unit has been mounted in a correct location for the patient and after the catherization procedure, the urinary collection bag 22 is taken to the AUOM unit 20 which is located outside of the sterile field of the catherization site and is mounted to the AUOM unit. The force isolation system 26 includes a relatively rigid header assembly 94 having a pair of spaced female connectors 96 and 98 which are adapted for mating receipt of mounting arms 46 and 48, respectively, to suspend the collection bag 22 therefrom. As will be explained in greater detail below with reference to FIG. 7, means are provided for causing arms 46 and 48 to interlock with female connectors 96 and 98.

Figure 3:
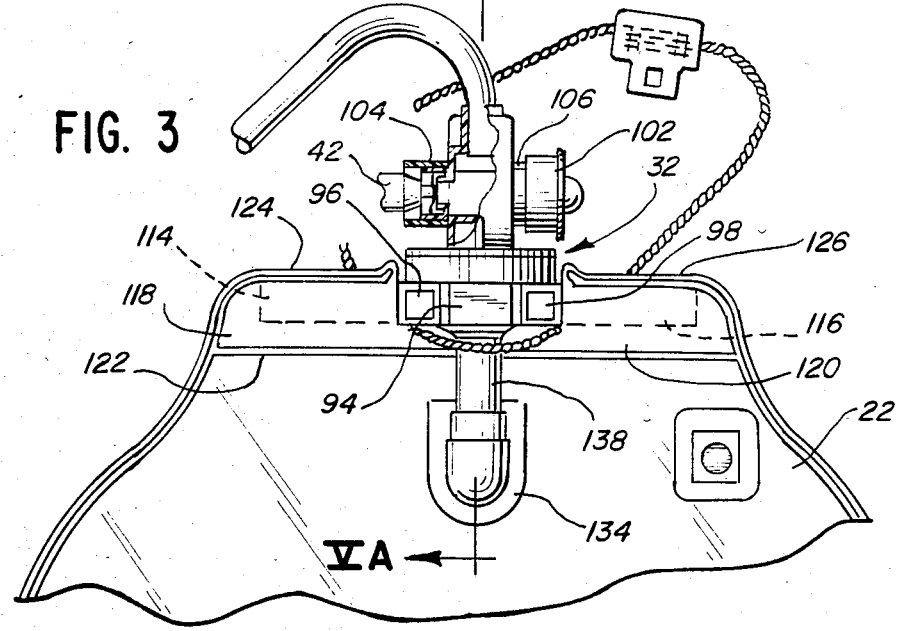
FIG. 3 is an enlarged front view of a header assembly and force isolation and sampling apparatus connected with the urinary collection.

After a pair of protective sensor caps 102, only one of which is shown in FIG. 3, are removed from a pair of probe guide connectors 104 and 106, the probe quide connectors 104 and 106 are enabled for mating receipt of sensor probe assemblies 42 and 44, respectively. Once caps 102 are removed, the sampling chamber assembly 24 is enabled for receipt within a sensing location 108 with sensor probe guide connectors 104 and 106 located respectively opposite sensor probes 42 and 44. The collection bag 22 is then locked onto arms 46 and 48.

The two sensor probe assemblies 42 and 44 are then caused to move together through manual actuation of a probe actuator 110. When the actuator 110 is moved from its position as shown in FIG. 1B to the operative position shown in FIG. 1A, the two sensor probes move together and respectively matingly engage the sensor probe guide connectors 104 and 106. Since the drainage tube 30 is mounted to sampling chamber assembly 24, both it and the downstream end of the drainage tube 30 are held against any movement relative to the housing frame 36. After this is done, the start switch 60 is actuated and the AUOM unit 20 begins operations to provide the monitor information described above.

The details of the force isolation system 26 and the sampling chamber assembly 24 are described with reference to FIGS. 3, 4, 5A, 5B, 6 and 7.

Figure 4:
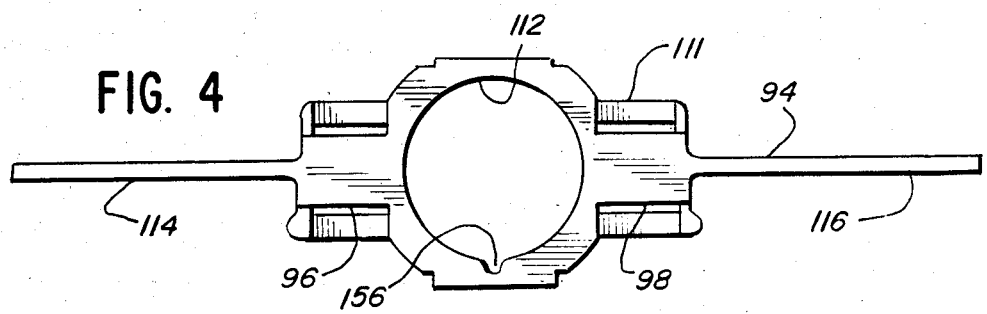
FIG. 4 is a plan view of the header assembly of FIG. 3.

Referring particularly to FIGS. 3 and 4, the header assembly 94 is seen to comprise a central body 111 with a central force isolation header connector 112 located between the pair of female connectors 96 and 98 together with a pair of opposed header mounting arms 114 and 116. The header is secured to the flexible bag 22 by means of a pair of header mounting pockets 118 and 120 within which are held mounting arms 114 and 116, respectively. These pockets are formed from extensions of the back and front walls 130 and 128 of urinary collection bag 22 which are secured together along a common seam 122 and a pair of upper seams 124 and 126 respectively associated with header mounting pockets 118 and 120. During manufacture, the header assembly 94 is placed in position with its header mounting arms 114 and 116 between the front and back walls of collection bag 22 prior to the formation of seams 124 and 126. Alternately, if sufficient clearance is provided or the relatively rigid header assembly arms 114 and 116 are sufficiently flexible, the arms 114 and 116 are inserted into pockets 118 and 120 after all the seams are formed.

Figure 5A:
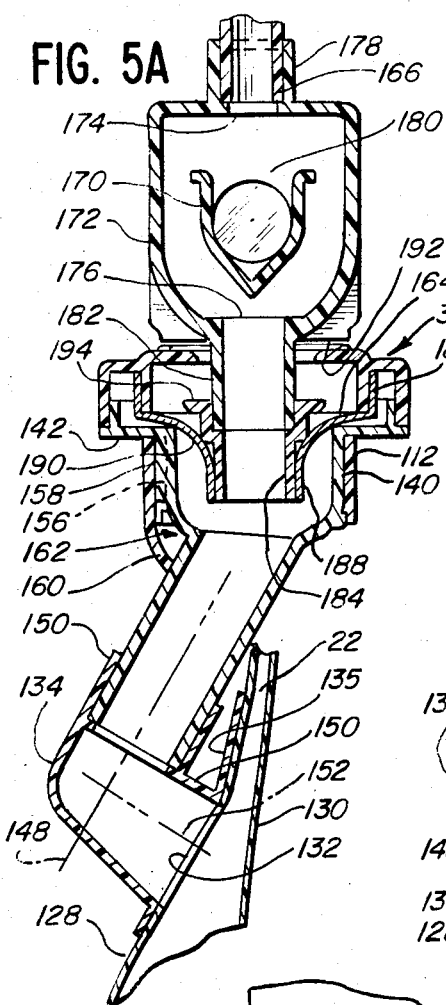
FIG. 5A is a sectional side view taken along section line VA—VA of FIG. 3.
Figure 5B:
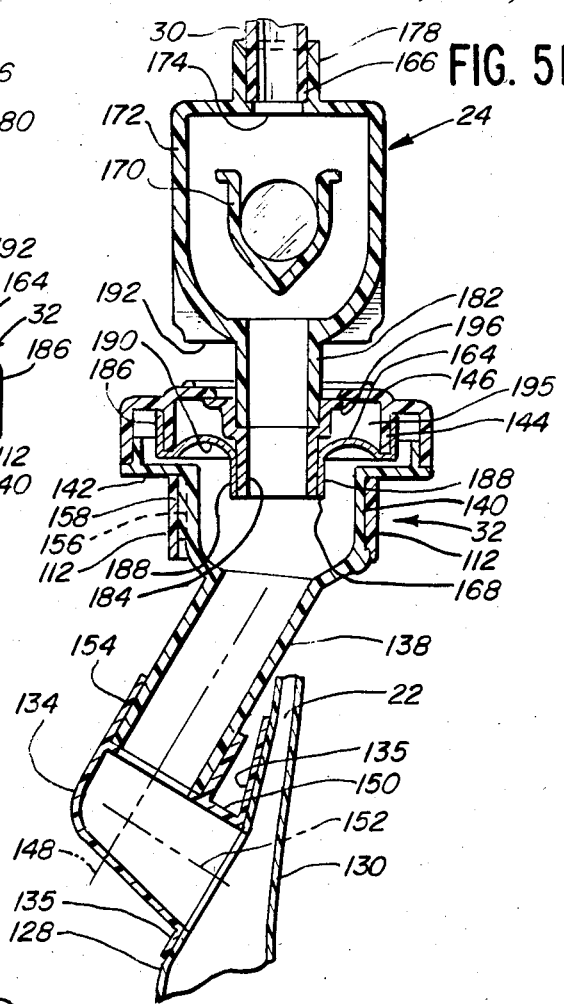
FIG. 5B is a sectional side view identical to that of FIG. 5A but with the header assembly in a relatively lower position due to increased weight of the collected urine.

Referring also to FIGS. 5A and 5B, a front wall 128, opposite a back wall 130 of urinary collection bag 22, is seen to have an inlet opening 132 in fluid communication with a coupler 134. Coupler 134 is sealed to the front wall 128 of flexible bag 22, by means of a flexible peripheral mounting collar 135 which is sealed to the front wall 128 around the periphery of inlet 132. A fluid conductive connector assembly, which forms part of the force isolation system 26, includes a downturned, elongate portion, or angular conduit, 138 for making fluid connection with the front 128 of the flexible bag 22 through coupler 134 and inlet 132. This angular conduit 138 is in fluid communication with a hopper portion 140 of relatively larger diameter, a shoulder 142, a flexible diaphragm mounting portion 144 and a movement restraint portion 146.

As seen, the angular conduit 138 extends at an acute angle relative to the back wall 130 of the collection bag 122. This enables it to make connection with the coupler 134 at a location offset from the central vertical plane of symmetry of the bag. This is the location that the portion adjacent coupler 134 of the wall 128 would move to as the bag 22 became full if there were not restraint on its movement. Otherwise during filling asymmetrical backward bulging of the collection bag 22 would result because of wall 128 being held at the vertical plane by the conduit 138.

This bulging would undesirably require more clearance between the AUOM housing panel 38 and the collection bag 22. The coupler 134 has a coupler axis 148 which extends in a direction substantially parallel to the front of the bag at the peripheral collar 135. A first member 150 has an axis 152 which extends at a right angle relative to the front of the bag at mounting collar 135. The connector portion 154 associated with axis 148, on the other hand, extends in a direction substantially transverse to that of the first portion 150 to form a right angle connection. As best seen in FIG. 5B, the axis 148 also forms an obtuse angle with the central axis of hopper portion 140 and connector 112.

During assembly, the angular conduit 138 and hopper portion 140 are received through the central force isolation connector 112. The header connector 112 is a cylindrical female connector for mating receipt of the cylindrical wall of the hopper portion 140. In order to prevent relative rotary movement, however, the cylindrical wall of header connector 112 has an interlock notch 156, as best seen in FIG. 4, which is adapted for mating receipt of a mating interlock member 158 seen in FIGS. 5A and 5B. The mating interlock member 158 is carried on the side wall of hopper portion 140 and is snugly received therein to prevent relative rotary movement between the hopper portion 140 and the central force isolation connector of header assembly 94. In addition, since only a single asymmetrically located interlock notch 156 and interlock member 158 are provided, the hopper portion 140 and the central force isolation header connector 112 are thereby keyed to require their intercoupling in a preselected orientation relative to the inlet 132.

After full insertion, the coupler 134 is pivoted upwardly for mating receipt of the open end of the angular conduit 138. After this connection is made, the interconnections between the connector 112 and hopper portion 140, connector 112 and shoulder 142 and connector portion 154 and the distal end of angular conduit 138, are rendered permanent by the application of adhesive, by setting of previously applied adhesive or by heat fusion or solvent bond.

Thus, the fluid conductive connector assembly 32 is permanently and fixedly attached to the urinary collection bag 22. It thereby forms a first relatively rigid connector for connecting one end of a highly flexible diaphragm, or conduit, 164 to form part of the force isolation system 26. As will be explained, the other part of the force isolation system comprises means for holding and interconnecting a downstream open end 166 of drainage tube 30 to the other end of flexible diaphragm 164 and for holding the drainage tube end 166 fixed relative to the housing frame 36.

In the instant case of the preferred embodiment, the relatively rigid connector for connecting the distal end 166 to the end 168 of the flexible diaphragm 164 includes a sampling chamber assembly 24 and means associated therewith. However, it should be appreciated that the sampling chamber function is not necessary to achieve force isolation and in the absence of such a chamber, a simpler connector may be employed for connection of the drainage tube downstream open end 166 to the upstream end of the flexible diaphragm.

Since the end 166 of drainage tube 30 is held firmly, the collection bag is isolated from force applied thereto. The high degree of flexibility of the diaphragm 164 prevents the connection thereof with the collection bag 22 from applying any significant restraint or other force thereto or to the weighing apparatus to which it is attached. Briefly, sampling chamber assembly 24, as seen, has a sampling chamber 170 contained within a sampling chamber housing 172 intermediate a housing inlet 174 and an outlet 176. The inlet 174 is connected in fluid communication with the open end 166 of drainage tube 30 by means of an annular inlet connector 178. After the flexible drainage tube 30 is inserted into mating relationship with connector 178, the connection is rendered permanent by means of applying adhesive, causing pre-applied adhesive to set, by solvent bond or the like. Urine dripping out of the inlet 174 falls into a combined inlet and outlet opening 180 of sampling chamber 170. After the sampling chamber 180 is filled, additional urine falling into the open top 180 will both mix with the previously collected urine in the sampling chamber and will cause other urine to overflow and fall through the outlet 176 and into hopper portion 140 of connector 136.

The outlet 176 is connected through an elongate conduit 182 interconnected at its distal end with a diaphragm connector 184. The flexible diaphragm 164 comprises a thin, flexible moisture impervious material, such as thin rubber, animal membrane, or the like, which forms part of a closed fluid collection system between the end 166 of drainage tube 30 and the collection bag 22. It has a relatively large inlet opening at the ends of a mounting collar 186 which is resiliently secured around the annular diaphragm mounting portion 144 of the connection assembly 32. At its other end, it has another annular collar 188, opening in a direction opposite to that of collar 186 and having a relatively smaller diameter to resiliently fit around the end of a diaphragm connector 184. A concave flexible wall interconnects collars 186 and 188.

The force isolation system 26 operates as follows. When the collection bag 22 is mounted to the header assembly 94, it is fixedly held to arms 46 and 48 which, in turn, are connected with a weight transducer which responds to the total force imposed upon arms 46 and 48. Ideally, this total force corresponds only to the weight of the fluid contained in the urinary collection bag 22 and the weight of the collection bag 22 itself which is known and can be offset to precisely calculate the weight of the urine alone. However, the urinary collection bag 22 must be connected to the end 166 of the drainage tube for receipt of the urine, and in the absence of a force isolation system, forces are imposed through the drainage tube 30 which are transmitted to arms 46 and 48 and thereby introduce error into the weight calculation.

The arms 46 and 48 are caused to move downwardly by the weight of the urine being collected, but the end 166 of drainage tube 30 is held stationary relative to the housing frame 36 of the AUOM unit 20 by means of the mating insertion of sensor probe guides 42 and 44 within guide connectors 104 and 106. Thus, forces applied to the end 166 of the drainage tube 30 are borne by the AUOM unit 20 and they are not transmitted to the header assembly 94. The flexible diaphragm 164 is then the only element which can transmit extraneous forces through the weighing mechanism. However, the flexible diaphragm is purposely selected to be so flexible that it is not capable of sustaining or supporting any significant forces either in a direction along its principal axis of movement coincident with the elongate axis of conduit 182. It can be maintained in a relatively stable state in any of several relative positions without transmitting any significant force along its length. Accordingly, the mounting arms 46 and 48 and collection bag 22 are free to move relative to the frame 36 in substantial isolation from any forces from the urinary delivery system from the patient to the collection bag 22.

Referring particularly to FIGS. 5A and 5B, when the collection bag 22 is first attached, the relative location of the mounting arms 46 and 48 relative to the sampling chamber assembly is as shown in FIG. 5A. As seen, the underside surface 192 of sampling chamber housing 172 rests atop restraint portion 146 of connection assembly 32. However, after the sensor probe assemblies 42 and 44 are engaged with the sampling chamber assembly 24, the underside surface 192 is held thereby slightly above restraint portion 146. However, as urine is added to the collection bag 22 and its weight increases, the mounting arms 46 and 48 and thus connector assembly 136 attached thereto, move downwardly away from an underside surface 192 of sampling chamber housing 172, causing the inlet opening at diaphragm collar 186 to move closer to the outlet opening at diaphragm collar 188. This relative movement is not significantly resisted by the concave wall 190 which forms a downwardly facing cuff within the space 195 between shoulder 142 and restraint portion 146, as shown in FIG. 5B, in response to this relative movement. This cuff moves along the length of the concave wall 190 of flexible diaphragm 164 as the connectors 144 and 184 are moved relative to one another.

Referring still to FIGS. 5A and 5B, particularly FIG. 5A, the diaphragm connector 184 carries a stop member 194 which is engageable in blocking relationship with the underside 196 of restraint portion 146 to restrain relative movement between the inlet and outlet connectors of the flexible diaphragm 164 beyond a preselected limit. Movement beyond this limit would cause the transmission of force to the header assembly 94 through means of the connector assembly 136 or which would stretch or otherwise damage the flexible diaphragm 164.

Figure 6:
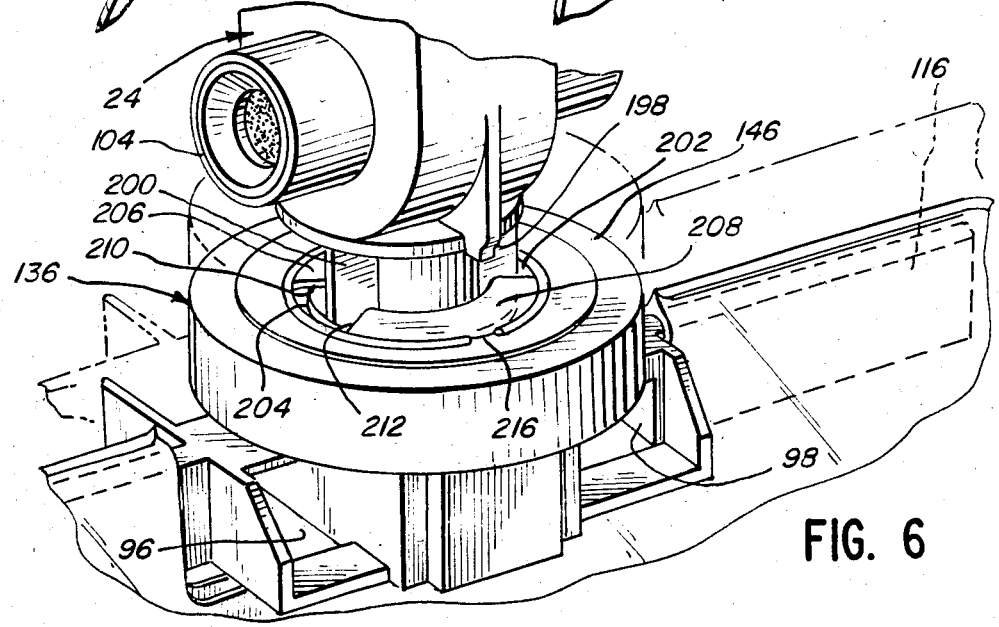
FIG. 6 is an enlarged perspective view of the force isolation and sampling chamber assembly of FIGS. 1A, 4, 5A and 5B.

As best seen in FIG. 6, the force isolation system 26 also includes means for restraining relative rotary movement between the ends of the flexible diaphragm which would twist it beyond a preselected limit. The rotary restraint is provided by means of a pair of radial blocking members 198 and 200 fixedly attached to the elongate conduit 182 of sampling chamber assembly 24 and received within a pair of slots 202 and 204. Slots 202 and 204 are formed by a pair of opposed arcuate sections 206 and 208 of restraint portion 146. Each of arcuate sections 206 and 208 define a pair of rotary blocking surfaces 210 and 212 at opposite sides of slots 204 and 202 which are spaced from one another by a preselected amount corresponding to the preselected limit. The blocking surfaces prevent the radial blocking members 198 and 200 associated therewith and thus the flexible diaphragm 164 from rotary movement beyond the preselected limit.

Figure 7:
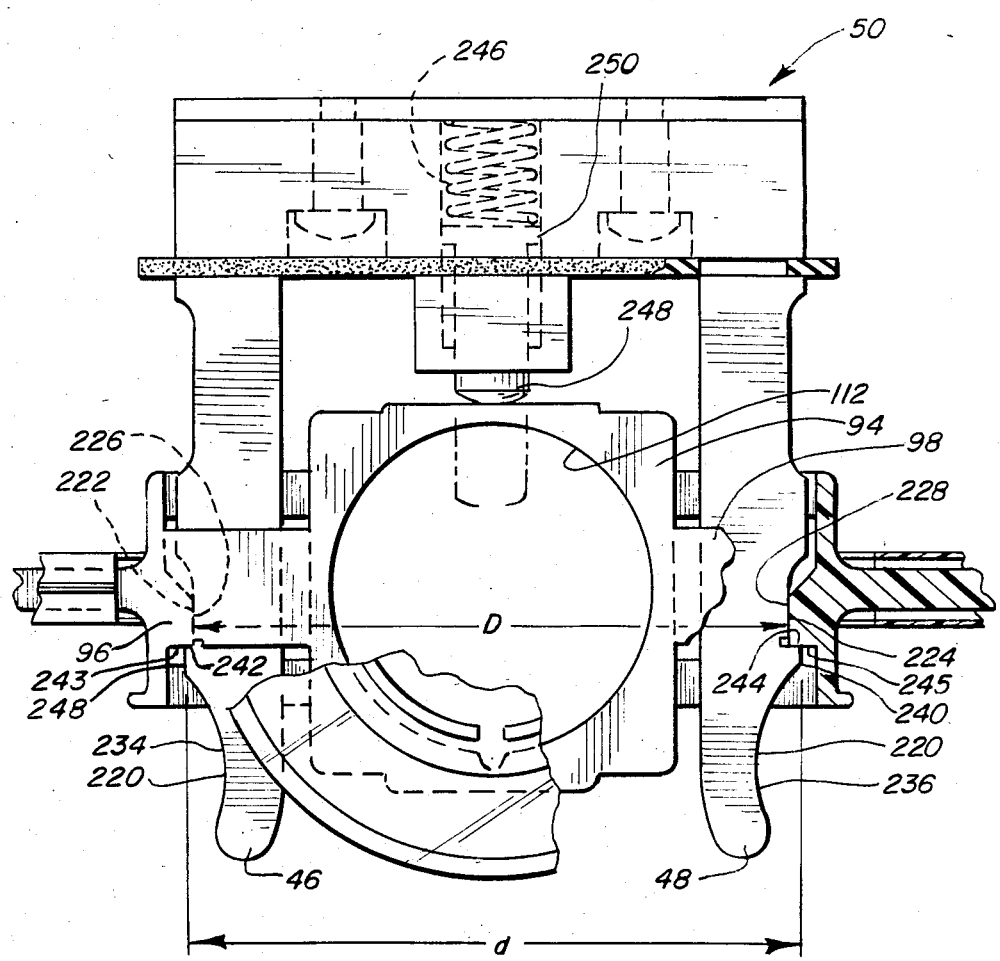
FIG. 7 is a plan view of the header mounting mechanism of FIG. 1B.

Referring now to FIG. 7, the detailed features of mating relationship between the female connectors 96 and 98 of header assembly 94 with the mounting arms 46 and 48 and other features of the bag mounting assembly 50 will be described. Each of the arms 46 and 48 are mirror images of one another and have a manually engageable portion 220 which extend through the associated female connector 96 and 98 for access at the front of the collection bag 22. Both of arms 46 and 48 are made of relatively resilient material and the distance d between a pair of outwardly facing planar cam surfaces 238 and 240 of arms 46 and 48, when in a neutral, or unflexed, condition, is greater than the distance D between a pair of inwardly facing interlock surfaces 226 and 228 of female connectors 96 and 98, respectively. A pair of shoulders 242 and 244 are formed at the edge of each of the outwardly facing planar cam surfaces 238 and 240 and a pair of interlock surfaces 222 and 224 of arms 46 and 48, respectively, which matingly receive the associated interlocking surfaces 226 and 228. When female connectors 96 and 98 are slid over the manually accessible portions 220 of arms 46 and 48, arcuate caming surfaces 234 and 236 carried thereby respectively engage interlock surfaces 222 and 224 and are thereby gradually, resiliently cammed together until the distance between outwardly facing planar cam surfaces 238 and 240 is equal to the distance D. The planar cam surfaces 238 and 240 then ride the interlock surfaces 226 and 228, respectively. When the lagging edges of interlock surfaces 226 and 228 pass shoulders 242 and 244, the arms 46 and 48 resiliently snap apart with the mating interlock surfaces joined as shown. The shoulders 242 and 244 then abut against the edge of their associated female connector interlock surfaces to prevent removal of the connectors from the arm. Thus, to mount the header assembly to arms 46 and 48, the female connectors only need to be slid on to their associated arms to automatically move them to an interlock position from their release position until the arms resiliently snap into the interlock position, as shown in FIG. 7. Once this occurs, a pusher member 248 resiliently pushes shoulders 243 and 245 of the female connectors against shoulders 242 and 244 of the arms.

The female connectors are automatically disengaged from the arms 46 and 48 when the manually engageable portions 220 of arms 46 and 48 are squeezed together sufficiently to move shoulders 242 and 244 out of blocking engagement. These shoulders, or blocking edges, 242 and 244 resist resilient biasing of the header assembly and female connectors thereagainst provided by a coil spring 246 associated with a pusher member 248 mounted within a cylindrical housing 250. This pusher member causes the female connectors 96 and 98 to automatically, slideably move off of interlocking engagement with arms 46 and 48 when the distance between cam surfaces 238 and 240 is less than the distance D between the interlock surfaces 226 and 228 of the connectors. Thus, the connectors are automatically disengaged from arms 46 and 48 simply by manually squeezing the manually accessible portions 220 together from the interlock position to the release position.

Figure 8A:
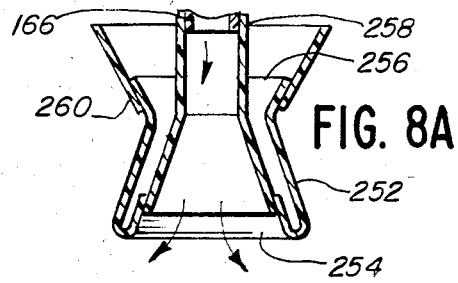
FIGS. 8A and 8B are schematic illustrations of an alternate embodiment of the force isolation system of FIGS. 5A and 5B under relatively unloaded and loaded conditions, respectively.
Figure 8B:
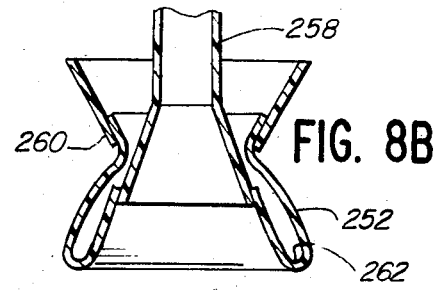

Referring to FIGS. 8A through 11B, alternate embodiments of the flexible diaphragm and associated connectors of the force isolation systems are schematically illustrated. In FIGS. 8A and 8B, a flexible diaphragm 252 is shown with an inlet 254 and outlet 256 of approximately the same diameter and which has substantially straight walls rather than concave walls, as in the preferred embodiment of FIGS. 4, 5A and 5B. An inlet connector 258 is held to the frame and connected to the drainage tube 166 and an outlet connector 260 is connected to the collection bag 22 (not shown). In addition, as best seen in FIG. 8A, 258 and 260 when the collection bag is relatively empty, the flexible diaphragm 252 forms a cuff 262 which faces upwardly toward the inlet connector 258. As the collection bag 22 fills, the outlet connector 260 moves downwardly closer to the inlet connector 258, as shown in FIG. 8B.

Figure 9A:
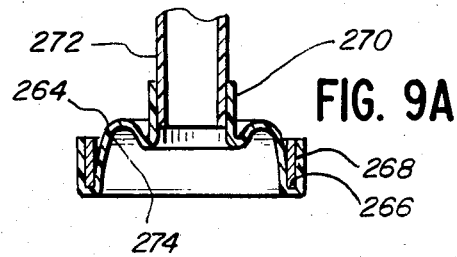
FIGS. 9A and 9B are schematic illustrations of another alternate embodiment of the force isolation system under relatively unloaded and loaded conditions, respectively.
Figure 9B:
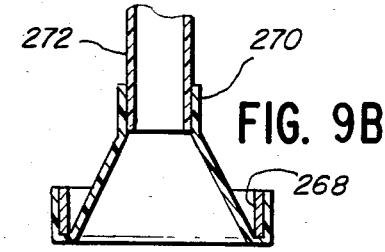

Referring to FIG. 9A and 9B, another embodiment of a flexible diaphragm 264 is shown under circumstances of a relatively empty and relatively full urinary collection bag 22, respectively. In this embodiment, the flexible diaphragm 264 has an upturned mounting cuff 266 which matingly receives an annular outlet connector 268 and the inlet end of flexible diaphragm 264 has a collar 270 connected to an inlet connector 272 of lesser diameter than outlet connector 268. A downwardly turned cuff 274 is formed in flexible diaphragm 264 which is gradually removed as the connectors 272 and 268 separate as shown in FIG. 9B until, at full extension, the flexible diaphragm 264 has a conical shape, as shown in FIG. 9B. Unlike the embodiments of FIGS. 8A and 8B and FIGS. 5A and 5B, the inlet is located above the outlet in the embodiment of FIGS. 9A and 9B.

Figure 10A:
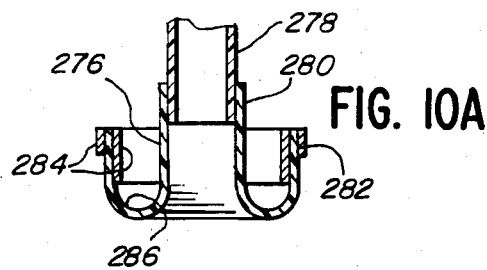
FIGS. 10A and 10B are schematic illustrations of a further alternate embodiment of the force isolation system under relatively unloaded and loaded conditions, respectively.
Figure 10B:
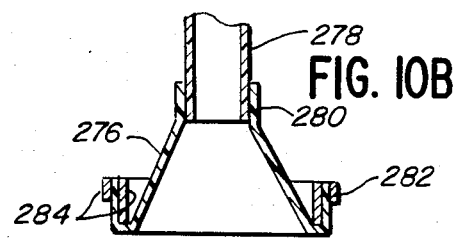

Referring now to FIGS. 10A and 10B, another embodiment of a flexible diaphragm 276 is shown in which an inlet end is connected to an inlet connector 278 by means of a collar 280, and the outlet end has a collar 282 which is held between a pair of outlet connector members 284. An upturned cuff 286 faces the inlet connector 278, and when the flexible diaphragm 276 is extended, as shown in FIG. 10B, the cuff 286 moves upwardly until a conical configuration is obtained, as shown.

Figure 11A:
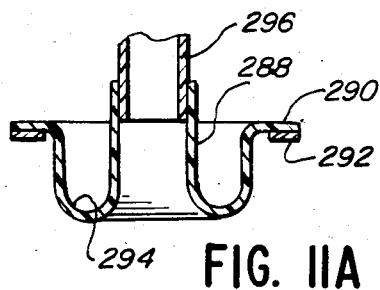
FIGS. 11A and 11B are cross sectional and perspective illustrations of still another alternate embodiment of the force isolation system.
Figure 11B:
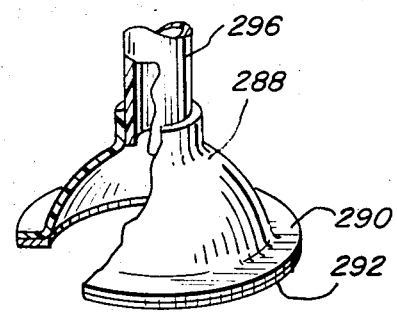

Referring now to FIGS. 11A and 11B, yet another embodiment of a flexible diaphragm 288 is shown similar to that of FIGS. 10A and 10B but in which the body of the flexible diaphragm is bell shaped when extended, as shown in FIG. 11B, and which has a laterally extending collar 290 attached to a laterally extending outlet connector 292 instead of the vertically extending collar and outlet connector of FIG. 10A. Like FIG. 10A, an upturned cuff 294 is formed when the inlet connector 292 and an outlet connector 296 are spaced from one another as shown in FIG. 11A.

Referring to FIG. 12, a schematic illustration of yet another embodiment of the force isolation system 26 is shown in which the flexible diaphragm 298 is generally cylindrical and does not form either an upturned or a downturned cuff, but merely folds in a random or accordian fashion, as shown. The outlet connector 300 directly attaches the outlet of the flexible diaphragm 298 to an inlet 302 of the flexible bag 22 located at the top 304 of the bag 22 rather than at its front wall 128. An inlet connector 306 is directly connected to the end 166 of the drainage tube 30. Relative lateral movement of the first and second connectors beyond a preselected limit is prevented by means including blocking arms 308, and relative rotary movement beyond a preselected limit is restrained by means including a pair of restraint members 310 which cooperate with radial vanes 312.

Advantageously, because of the improvement of accuracy obtained as a result of the force isolation system, an improved method of weighing urine collected from a patient is provided. In prior weighing systems, because of the unknown magnitude of extraneous forces applied to the collection bag and weighing apparatus by the urine delivery system, urine entered into the collection bag upon catherization and before mounting of the collection bag to the weighing apparatus, was not accurately weighed. It is not accurately weighed in prior devices because of the need of first zeroing the weighing apparatus to insure the degree of accuracy needed for flow rate and other measurements. Offsetting the determined weight before attachment of the bag to zero the weighing apparatus for empty bag weight is preferred. However, in the method provided here, the step of zeroing after mounting the collection bag is eliminated, so that the urine collected prior to mounting may be accurately weighed and volume determined.

In particular, a method for weighing a volume of fluid is provided comprising the steps of (a) predetermining the weight of the urine collection bag 22 based on an average bag weight of a large sample of substantially identical bags, (b) offsetting the determinant weight of the bag 22 from the weighing apparatus of the AUOM unit 20, (c) connecting the downstream end 166 of the drainage tube 30 to an inlet 132 of bag 22 by means including the force isolation system 26 to substantially mechanically isolate the bag 22 and the weighing apparatus to which it is connected from forces due to the interconnection of the bag 22 and the end 166 of tube 30, (d) attaching the bag 22 to the bag mounting assembly 50 to be weighed, and (e) entering the urine to be weighed into the bag 22 through tube 30 and the force isolation system 26.

Thus, the urine which may enter the collection bag 22 before the bag 22 is attached to the bag mounting assembly 50 is weighed because the weighing apparatus is not zeroed to cancel out the weight of this previously collected urine. Accordingly, the AUOM unit weighs it together with the urine subsequently collected to give a combined weight or volume indication.

While a particular embodiment has been shown, it should be appreciated that variations may be made with regard thereto without departing from the scope of the invention. For instance, although a flexible plastic bag 22 has been disclosed for collecting urine, it should be clear that many of the advantageous features of the invention could be successfully employed with rigid fluid containers or container and collection systems for other types of biological fluids, such as blood. Thus, the scope of the invention is defined by the following claims and not by the foregoing detailed description of the preferred embodiment.

I claim:

1. Apparatus for measuring the weight of fluid entering a container of a system obtained from the downstream end of a fluid drainage tube, comprising:

a weighing apparatus having a frame and a weighing mechanism which moves relative to the frame during changes of the weight being weighed thereby;

means for connecting the container to the weighing mechanism to be weighed thereby, said container moving with the weighing mechanism relative to the frame as increasing amounts of fluid are introduced into the container;

means for holding the downstream end of the tube against movement relative to the frame; and means for coupling the drainage tube with the container for relative fluid communication therewith including means for substantially mechanically isolating the end of the tube from application of significant force to the container whereby the accuracy of the measurement of the weight of the container and its contents is not significantly affected by the coupling means.

2. The apparatus of claim 1 in which said isolation means includes a flexible member interconnecting the end of the drainage tube to the container.

3. The apparatus of claim 2 in which said isolation means includes a pair of relatively rigid connector members for respectively connecting opposite ends of the isolation means to an opening in the container and to the end of the drainage tube.

4. The apparatus of claim 3 in which the one of the connectors connecting the isolation means to the drainage tube is a connector for mating connection with the downstream end of the drainage tube.

5. The apparatus of claim 1 in which
said container is a flexible bag, and
said connecting means includes means attached to the one of said pair of connectors for suspending the bag from the weighing mechanism to move therewith.

6. The apparatus of claim 1 in which said isolation means includes
a first relatively flexible member secured to the container and having an inlet opening therethrough, and
a second conduit interconnecting the end of the tube to the inlet opening.

7. The apparatus of claim 6 in which
said container is a flexible bag, and
said first relatively flexible member has greater flexibility than most of the bag.

8. The apparatus of claim 6 in which said connecting means includes
a relatively rigid connector which is fixedly attached to the container and substantially surrounds said first relatively flexible member, and
means for releasible connection of the connector to the weighing apparatus.

9. The apparatus of claim 1 in which the conduit is substantially cylindrical.

10. The apparatus of claim 1 in which said container is a flexible bag with a top and a front and said coupling means couples the drainage tube to an inlet opening at the top of the bag.

11. The apparatus of claim 1 in which said isolating means comprises means for flexibly coupling the end of the drainage tube to the container.

12. The apparatus of claim 1 in which said weighing apparatus includes a transducer responsive to force applied to it to produce a representative electrical signal.

13. A container assembly for biological fluids, comprising:
a hollow container body having an inlet opening for receipt of fluids therewithin,
an inlet connector for connection with the end of a drainage tube, and
means for substantially mechanically isolating the container body at the inlet opening from relative movement of the inlet connector, said isolating means including a flexible conduit for interconnecting the inlet connector and the inlet opening, said conduit having a flexibility sufficient to prevent it from mechanically conveying significant force in a direction along the conduit.

14. The container assembly of claim 13 in which said container body is a flexible plastic bag.

15. The container assembly of claim 14 including a mounting member associated with the isolation means and attached to the container body for mounting it to a fixture.

16. The container assembly of claim 15 in which said mounting member has means for suspending it, and thus the container body, from a fixture.

17. The container assembly of claim 15 in which said mounting member is attached to the container body adjacent the inlet opening.

18. The container assembly of claim 17 in which said mounting member has means for suspending it and thus the container body from a fixture.

19. The container assembly of claim 13 in which the flexible conduit is substantially non-resilient.

20. The container assembly of claim 13 in which the flexible conduit is substantially resilient.

21. The container assembly of claim 13 in which said container body is a flexible bag with a top and a front and said inlet is at the top.

22. The container assembly of claim 13 including a weighing apparatus having a transducer responsive to force applied to it for providing a signal representative of weight.

23. A method of weighing a volume of fluid, comprising the steps of:
predetermining the weight of a fluid container;
offsetting the determined weight of the container from a weighing apparatus to zero the weighing apparatus;
connecting the downstream end of a drainage tube to an inlet opening of the fluid container by means for substantially mechanically isolating the container and the weighing apparatus from forces due to the interconnection of the container and the end of the tube;
attaching the container to the weighing apparatus to be weighed thereby;
entering the fluid to be weighed into the container through the drainage tube and said isolation means; and
weighing the container and fluid therein.

24. The method of claim 23 including the steps of
entering some of the fluid into the container after determining the amount of off-set to zero the weighing apparatus to compensate for the weight of the container and before the step of attaching the container to the weighing apparatus to be weighed thereby, and
then obtaining from the weighing apparatus the combined weight of the fluid entered into the container before and after the step of attaching the container to the weighing apparatus prior to further zeroing of the weighing apparatus.

25. The method of claim 24 in which said step of entering some of the fluid into the container includes the step of connecting the upstream end of the drainage tube in fluid communication with an in vivo fluid source.

26. The method of claim 25 in which said step of connecting the upstream end of the drainage tube includes insertion of a urinary catheter.

* * * * *